United States Patent [19]

Möckl

[11] Patent Number: 5,343,109
[45] Date of Patent: Aug. 30, 1994

[54] ULTRASONIC TRANSDUCER FOR MEASURING THE TRAVEL TIME OF ULTRASONIC PULSES IN A GAS

[75] Inventor: Thomas Möckl, Coburg, Fed. Rep. of Germany

[73] Assignee: Siemens Aktiengesellschaft, Munich, Fed. Rep. of Germany

[21] Appl. No.: 27,716

[22] Filed: Mar. 8, 1993

[30] Foreign Application Priority Data

Sep. 6, 1990 [DE] Fed. Rep. of Germany ....... 4028315

[51] Int. Cl.$^5$ ...................... H01L 41/08; G01N 29/00
[52] U.S. Cl. .................................. 310/334; 310/317; 310/327; 73/597; 73/644
[58] Field of Search ............... 310/317, 327, 328, 334, 310/336; 73/644, 597

[56] References Cited

U.S. PATENT DOCUMENTS

| | | | |
|---|---|---|---|
| 3,362,501 | 1/1968 | Lenahan | 181/141 |
| 3,921,442 | 11/1975 | Soloway | 310/328 |
| 4,160,229 | 7/1979 | McGough | 340/7 R |
| 4,414,482 | 11/1983 | Lewis et al. | 310/334 |
| 4,446,395 | 5/1984 | Hadjicostis | 310/327 |
| 4,507,582 | 3/1985 | Glenn | 310/327 |
| 4,523,127 | 6/1985 | Ioue et al. | 310/334 |
| 4,556,814 | 12/1985 | Ito et al. | 310/334 |
| 4,680,499 | 7/1987 | Umemura et al. | 310/334 |
| 4,733,379 | 3/1988 | Lapetina et al. | 367/20 |
| 4,809,243 | 2/1989 | Bledsoe et al. | 367/154 |
| 4,976,150 | 12/1990 | Deka | 76/644 |
| 5,053,668 | 10/1991 | Mitsuyasu | 310/317 |
| 5,121,628 | 6/1992 | Merkel et al. | 73/290 V |

FOREIGN PATENT DOCUMENTS

| | | | |
|---|---|---|---|
| 0130709 | 1/1985 | European Pat. Off. | G01K 11/02 |
| 0305519 | 3/1989 | European Pat. Off. | H04R 17/00 |
| 0119855 | 5/1989 | European Pat. Off. | G01K 11/02 |
| 3430161 | 2/1986 | Fed. Rep. of Germany | 310/334 |
| 3832947 | 3/1990 | Fed. Rep. of Germany | G01H 17/00 |
| 0738941 | 10/1955 | United Kingdom | 73/644 |
| 9204134 | 3/1992 | World Int. Prop. O. | |

OTHER PUBLICATIONS

"Ultrasonic Linear Array Probe with Triple Acoustic Matching Layers"; Proceedings of 6th Imposium on Ultrasonic Electronics; Tokyo 1985; Japanese Journal of Applied Physics, vol. 25 (1986) Supplement 25-1, pp. 82-84.

IEEE Transactions on Ultrasonics, Ferroelectrics, and Frequency Control, vol. UFFC-33, No. 6, Nov. 1986, "New Method of Time Domain Analysis of the Performance of Multilayered Ultrasonic Transducers", pp. 669-678.

Japanese Journal of Applied Physics, vol. 23, No. 6, Jun. 6, 1984, pp. L436-L438 "High-Frequency Ultrasonic Transducer Operating in Air".

Primary Examiner—Thomas M. Dougherty
Attorney, Agent, or Firm—Herbert L. Lerner; Laurence A. Greenberg

[57] ABSTRACT

An ultrasonic transducer for measuring the travel time of ultrasonic pulses in a gas, in particular for a gas flow rate meter, includes a piezoelectric radial oscillator, which is preferably formed a piezoceramic and which has two sides and electrodes each being disposed on a respective one of the sides for receiving a spike pulse voltage. A first adaptation layer is applied to one of the sides of the radial oscillator. The first adaptation layer has a thickness being less than one-fourth of a characteristic wavelength of the transducer. A second adaptation layer is applied to the first adaptation layer. The second adaptation layer also has a thickness being less than one-fourth of the characteristic wavelength of the transducer. A damping body is mounted on the other of the sides of the radial oscillator. The radial oscillator and the adaptation layers form a sandwich executing a thickness oscillation as a consequence of a radial-thickness coupling, as soon as the spike pulse voltage is applied. The characteristic wavelength of the transducer is a wavelength resulting from natural resonance in the thickness oscillation.

17 Claims, 1 Drawing Sheet

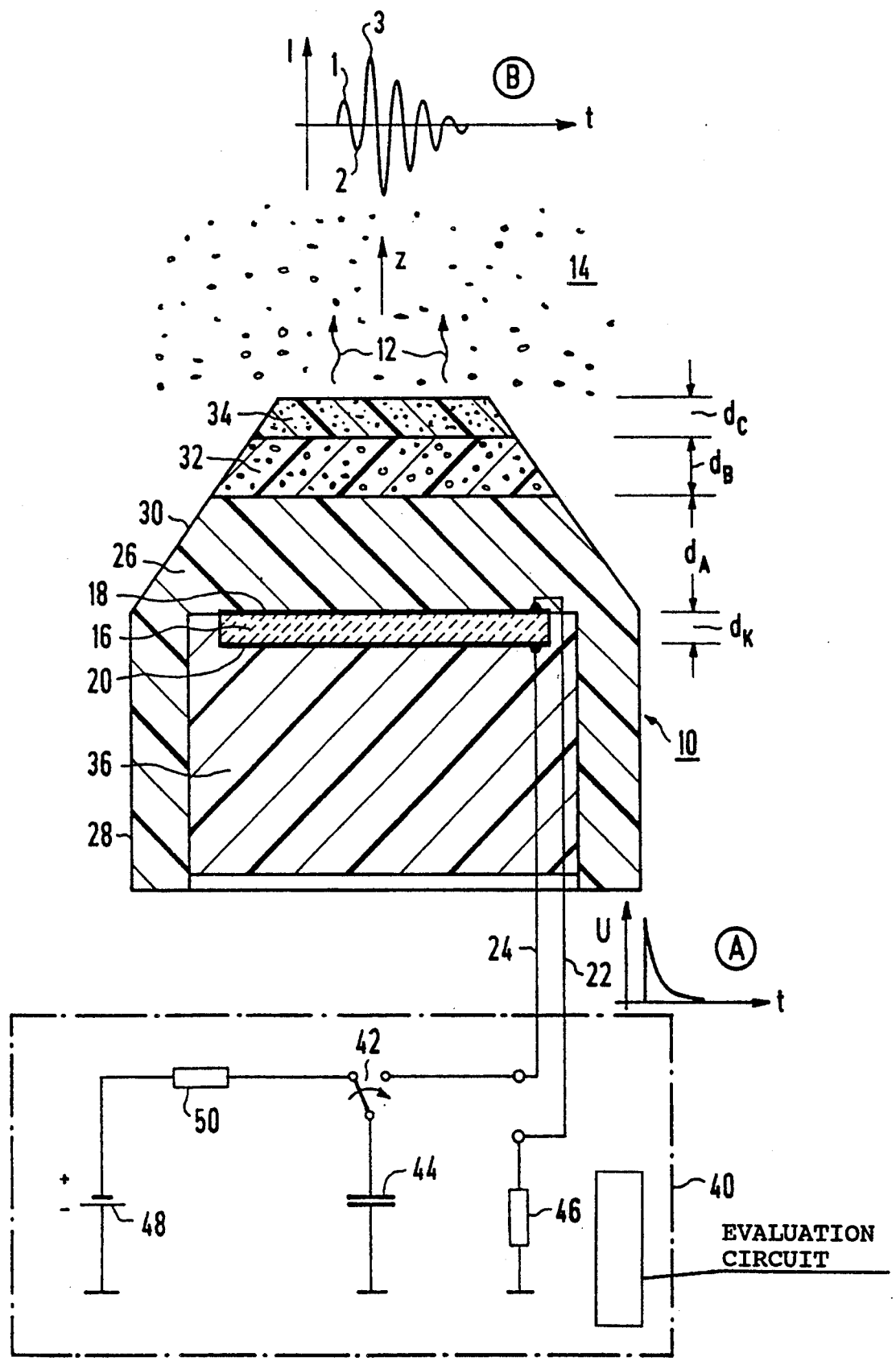

ULTRASONIC TRANSDUCER FOR MEASURING THE TRAVEL TIME OF ULTRASONIC PULSES IN A GAS

CROSS-REFERENCE TO RELATED APPLICATION

This application is a continuation of International Application Ser. No. PCT/DE91/00614, filed Jul. 31, 1991.

SPECIFICATION

The invention relates to an ultrasonic transducer for measuring the travel time of ultrasonic pulses in a gas, in particular for a gas flow rate meter. The invention can be preferentially used as a gas counter for measuring the quantity of natural gas, or as an air flow rate meter. Such air flow rate meters can be used in conjunction with heating systems, for instance.

Ultrasonic transducers having a piezoelectric oscillator, in particular a piezoceramic, for measuring the travel time of ultrasonic pulses in a gas, differ fundamentally from ultrasonic transducers in which the ultrasonic pulses are sent into water or into human tissue, because of the differing impedance. Methane, for instance, has an impedance of 260 kg/s²m, while human tissue has an impedance of $1.5 \cdot 10^6$ kg/s²m. By comparison, piezoceramic has an impedance of approximately $2.2 \cdot 10^7$ kg/s²m. In order to obtain good transformation of the piezoceramic oscillator typically used in the ultrasonic transducer to the gas, different aspects must accordingly be taken into account from those involved in transformation into water or tissue.

In a gas flow rate meter that operates by the principle of measuring the travel time of ultrasonic pulses, a suitable ultrasonic or pulse transducer is needed that can be excited with a spike voltage pulse. That kind of spike voltage pulse can be generated by a capacitor discharge, for instance. After passing through the gas to be measured, then only the wave front, and at most the first three half-waves, of the ultrasonic pulse reaching an evaluation circuit should be evaluated, in order to avoid interference.

German Published, Non-Prosecuted Application DE 38 32 947 A1 discloses an ultrasonic transducer for gas measurement that uses a piezoceramic disk provided with electrodes on both sides, as its oscillator. That disk has a diameter of 10 mm and a thickness of 1 mm, for instance. A plastic filled with hollow glass beads is used as an adaptation layer, for adaptation to the gas to be measured. The adaptation layer is constructed as a cup-shaped housing, and the piezoceramic disk is glued to the inside of the cup, on its bottom. It is significant in that case that the cup bottom is constructed as a λ/4 transformation layer, which is tuned approximately to the dominant resonance (planar oscillation) of the piezoceramic disk. The dominant resonant frequency is approximately 195 kHz. In order to enable maximum energy transport of the ultrasonic pulses generated by such an ultrasonic transducer into the gas, it suffices to use a material of low damping and high strength, having an impedance $Z_M$ which meets the condition $$Z_M = (Z_K \times Z_G)^{\frac{1}{2}} \tag{1}$$

in which $Z_K$ is the impedance of the piezoceramic disk, and $Z_G$ is the impedance of the gas. Such a construction has the disadvantage of only allowing low tolerances with respect to the impedance $Z_N$ of the material and the thickness $d_N$ of the λ/4 transformation layer. That limits the selection of material, on one hand, and on the other hand, the production of the adaptation layer requires high-precision work.

European Patent No. 0 119 855 B1, corresponding to U.S. Pat. No. 4,523,122, particularly FIG. 12, teaches that in an ultrasonic transducer it is also possible to use two adaptation layers, which are disposed one above the other and are of differing acoustical impedance, on the same piezoelectric thickness oscillator.

However, in that process, it is assumed that both layers are constructed as λ/4 layers, and as a result they are subject to the tolerance requirements discussed above.

German Published, Non-Prosecuted Application DE 35 05 852 C, corresponding to U.S. Pat. No. 4,556,814, discloses accommodating an ultrasonic oscillator, provided with electrodes on both sides, in a cup-shaped housing. The bottom of the housing, acting as a radiating surface, is formed of a porous plastic, particularly an epoxy resin.

U.S. Pat. No. 4,414,482 discloses the possibility of exciting an ultrasonic transducer in the nonresonant range as well. However, that ultrasonic transducer is an array that is likewise used in the medical field for examining human tissue.

It is accordingly an object of the invention to provide an ultrasonic transducer for measuring the travel time of ultrasonic pulses in a gas, which overcomes the hereinaforementioned disadvantages of the heretofore-known devices of this general type, which outputs the highest possible sound or impact wave after a spike pulse for electrical excitation and in which it should be unnecessary to adhere to stringent tolerances for its production.

With the foregoing and other objects in view there is provided, in accordance with the invention, an ultrasonic transducer for measuring the travel time of ultrasonic pulses in a gas, in particular for a gas flow rate meter, comprising a piezoelectric radial oscillator, preferably of a piezoceramic, having two sides, electrodes each being disposed on a respective one of the sides for receiving a spike pulse voltage; a first adaptation layer being applied to one of the sides of the radial oscillator, the first adaptation layer having a thickness being less than one-fourth of a characteristic wavelength of the transducer; a second adaptation layer applied to the first adaptation layer, the second adaptation layer also having a thickness being less than one-fourth of the characteristic wavelength of the transducer; a damping body mounted on the other of the sides of the radial oscillator; and the radial oscillator and the adaptation layers forming a sandwich executing a thickness oscillation as a consequence of a radial-thickness coupling, as soon as the spike pulse voltage is applied, and the characteristic wavelength of the transducer being a wavelength resulting from natural resonance in the thickness oscillation.

In such an ultrasonic transducer, the two adaptation layers are accordingly not constructed as λ/4 layers. It is therefore unnecessary to meet extreme tolerances. This is based on the recognition that a nonresonant impedance adaptation has virtually no influence on the first three half-waves of the ultrasonic pulse transmitted as a result of a spike voltage pulse.

In accordance with another feature of the invention, the first adaptation layer is in the form of a cup having a bottom, and the radial oscillator is disposed on the bottom of the cup.

In accordance with a further feature of the invention, the cup is filled with the damping body. This assures that after the excitation, the radial oscillator can change to the position of repose without excessive post-pulse oscillation.

In accordance with an added feature of the invention, the cup has a flattened surface in the vicinity of the bottom.

In accordance with an additional feature of the invention, there is provided a third adaptation layer disposed over the second adaptation layer.

In accordance with yet another feature of the invention, the thickness $d_A$ of the first adaptation layer is selected as $\lambda/8 \leq d_A < \lambda/4$, the thickness $d_B$ of the second adaptation layer is selected as $\lambda/8 \leq d_B < \lambda/4$, and $\lambda$ is the wavelength of the thickness oscillation.

In accordance with yet a further feature of the invention, the thicknesses $d_A$ and $d_B$ of the first and second adaptation layers follow the statement $d_A + d_B \approx \lambda/4$.

In accordance with yet an added feature of the invention, the thicknesses $d_A$ and $d_B$ of the first and second adaptation layers and the thickness $d_k$ of the radial oscillator follow the statement $d_A + d_B + d_K \leq \mu/2$.

In accordance with yet an additional feature of the invention, the first adaptation layer is a layer of glass microbeads in epoxy resin.

In accordance with again another feature of the invention, the second adaptation layer is an open-cell foam.

In accordance with again a further feature of the invention, there is provided an electric excitation circuit for applying the spike pulse voltage to the electrodes, the electric excitation circuit including a capacitor discharging to the electrodes upon being activated.

In accordance with again an added feature of the invention, there is provided an evaluation circuit evaluating at most a first three half-waves of each of the ultrasonic pulses tripped upon excitation, after each pulse passes through the gas.

In accordance with a concomitant feature of the invention, the transducer is constructed for a frequency of approximately 200 kHz.

Other features which are considered as characteristic for the invention are set forth in the appended claims.

Although the invention is illustrated and described herein as embodied in an ultrasonic transducer for measuring the travel time of ultrasonic pulses in a gas, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawing.

The drawing is diagrammatic, sectional view of an ultrasonic transducer and a schematic diagram of an electric excitation circuit, according to an exemplary embodiment of the invention.

Referring now to the single FIGURE of the drawing in detail, there is seen an ultrasonic transducer 10 for measuring the travel or transit time of ultrasonic pulses 12 that are radiated into a gas 14 in a direction z. The gas 14 may in particular be city gas or natural gas, but it may also be methane. The course of an intensity I of a transmitted ultrasonic pulse is shown in a diagram B as a function of time t. In order to avoid interference, the measurement principle, which is known per se, evaluates at most the first three half-waves 1, 2 and 3 of the ultrasonic pulse I(t) that is shown.

The core piece of the ultrasonic transducer 10 is a piezoelectric oscillator 16, which is preferably made of a piezoceramic. This ultrasonic oscillator 16 may in particular be a piezoceramic disk with a diameter of 10 mm and a thickness of 1 mm. This ultrasonic oscillator 16 is provided with metal electrodes 18, 20 on both sides, and a spike pulse voltage U(t) can be applied to these electrodes through feed lines 22, 24. The course of this voltage U(t) over time is shown in a diagram A. The ultrasonic oscillator 16 in particular is a piezoelectric radial oscillator, because such an oscillator converts the radial oscillation which is generated as a consequence of the application of the spike pulse voltage U(t), into an oscillation in the z direction, as a consequence of what is known as radial-thickness coupling.

A first adaptation layer 26 is applied to the upper surface of the radial oscillator 16. This first adaptation layer 26 is the bottom of a cup 28. The radial oscillator 16 is disposed symmetrically in the interior of this cup. In the region of its bottom, the cup 28 is flattened on the outside or is provided with a conical flattening or bevel 30. The thickness $d_A$ of the first adaptation layer 26 is less than one-fourth of a wavelength $\lambda$ characteristic of the transducer. In particular, the thickness $d_A$ is selected as $$0.125\lambda \leq d_A < 0.2\lambda. \tag{2}$$

A second adaptation layer 32 of a different material is applied over the first adaptation layer 26. It is likewise beveled at the edge.

The thickness $d_B$ of this second adaptation layer 32 is likewise less than one-fourth the aforementioned wavelength $\lambda$ characteristic of the transducer. In particular, once again the following selection can be made:

$$0.125\lambda \leq d_B < 0.2\lambda. \tag{3}$$

A third adaptation layer 34 with a thickness $d_C$ can also be applied over the second adaptation layer 32. The task of the adaptation layers 26 and 32 and optionally 34 is to adapt the impedance $Z_K$ of the piezoceramic disk 16 to the impedance $Z_G$ of the gas 14.

As is noted above, the thicknesses $d_A$, $d_B$ of the adaptation layers 26, 32 are less than one-fourth the characteristic wavelength $\lambda$ of the transducer. This dimensioning is performed at the cost of what is known as "phase maladaptation". It must be pointed out that the term "maladaptation" applies in this case only to the case of the resonance. It was in fact recognized that a "resonant impedance adaptation" by $\lambda/4$ transformation or adaptation layers makes sense only whenever the ultrasonic transducer 10 is fully capable of transient response, so that the resonance advantage gained by quality is utilized. In this case, the advantages from resonance advantage are ineffective, because only the wavefront of the ultrasonic pulse is evaluated. In the present case, in which only the first three half-waves 1, 2 and 3, at most, are utilized for evaluation purposes, the "maladaptation" does not play any significant role in the outcoupling of energy into the gas 14. As a rule, it is even possible to make do with only two wave trains. Preferably, the thicknesses $d_A$ and $d_B$ can therefore each be between one-eighth and one-fourth of the aforementioned characteristic wavelength $\lambda$ of the transducer. In this regard reference should be made to equations (2) and (3). It has been demonstrated to be advantageous for the sum of these two thicknesses, namely $d_A + d_B$ to be approximately one-fourth of the aforementioned wavelength $\lambda$. In other words, $$d_A + d_B \leq \lambda/4. \tag{4}$$

If the thickness $d_K$ of the piezoceramic 16 is also included in the observation, then an advantageous embodiment is attained if the following relationship is adhered to:

$$d_A + d_B + d_K \leq \lambda/2. \tag{5}$$

A damping body or ultrasonic sink 36 is disposed on the lower surface of the radial oscillator 16. The damping body 36 is located inside the cup 28. In other words, the cup 28 is almost entirely filled by the damping body 36.

As soon as the spike pulse voltage U(t) of the diagram A is applied to the electrodes 18, 20, the sandwich made up of the radial oscillator 16 and the two adaptation layers 26, 32, and optionally the third adaptation layer 34, executes a thickness oscillation in the z direction, as a result of what is known as radial-thickness coupling. Due to the natural resonance in the thickness oscillation, the result is a wavelength that is the aforementioned characteristic wavelength $\lambda$ of the transducer. The natural resonant frequency may be in the range of 200 kHz.

In the case of double adaptation by means of the two layers 26, 32, an impedance $Z_K = 2 \cdot 10^7$ kg/s²m can be selected by way of example for the piezoelectric radial oscillator 16, which preferably may be formed of lead zirconate titanate. The impedance $Z_A$ of the first adaptation layer 26 may then be $1.35 \cdot 10^6$ kg/s²m and the impedance $Z_B$ of the second adaptation layer 32 may be $1.0 \cdot 10^5$ kg/s²m, for instance. The impedance $Z_G$ of methane (natural gas) is equal to 260 kg/s²m.

A layer of glass microbeads in epoxy resin may, for instance, be provided as the first adaptation layer 26. An open-cell foam, or foamed polystyrene, for instance instead, may be used as the second adaptation layer 32. Materials, having an acoustical impedance of $Z_B = 1 \cdot 10^5$ kg/s²m include polyurethane foams or cork. Model-making foam may also be used. The third adaptation layer 34 may also in principle be formed of a foamed polystyrene ($Z = 4.43 \cdot 10^3$ kg/s²m).

In order to provide triple adaptation with the three layers 26, 32, 34, the following values, for instance, can be selected:

$$Z_A = 1.3 \cdot 10^6; Z_B = 8 \cdot 10^4; Z_C = 4.5 \cdot 10^3 \text{ kg/s}^2\text{m}.$$

Another combination of values would be the following:

$$Z_A = 2.5 \cdot 10^6; Z_B = 1.25 \cdot 10^6; Z_C = 1.0 \cdot 10^5 \text{ kg/s}^2\text{m}.$$

The values $d_A = 2.3$ mm, $d_B = 1.5$ mm and $d_C = 1.0$ mm may be selected for a characteristic transducer frequency $f = c/\lambda = 200$ kHz.

It must be remembered that not only the impedances Z but also the thicknesses d need not precisely match previously calculated values in order to attain out-coupling of energy. Pronounced tolerances are allowable, making for considerable freedom in the selection of materials and in the accuracy of manufacture.

In order to apply the spike pulse voltage U(t) to the electrodes 18, 20, an electric excitation circuit 40 is provided. As its essential element, the circuit 40 includes a reversing switch 42, with which a discharging of a capacitor 44 is brought about. Upon switchover of the switch 42, this capacitor 44 discharges to the electrodes 18, 20. A discharging resistor 46, which may also be provided as the lines 22, 24, is provided in the discharge path. In order to charge the capacitor 44 through the reversing switch 42, a charging circuit is provided, which may include a direct voltage source 48, of 300 V, for instance, and a charging resistor 50. In a departure from the basic illustration in the drawing, the reversing switch 42 may be constructed as one or more thyristors.

An evaluation circuit is known per se. It is constructed in such a way that it evaluates at most the first three half-waves 1, 2, 3, and preferably only the first two half-waves 1 and 2, of each of the ultrasonic pulses I(t) tripped upon excitation, after the pulse has passed through the gas 14. The quantity of the gas stream 14 moving past the ultrasonic transducer 10 can be determined from the travel time.

The advantage of the ultrasonic transducer which is shown is that after an electrical excitation pulse U(t) in accordance with the diagram B, it outputs a high-intensity sound or impact wave, without requiring particularly stringent adherence to tolerances for the values d and Z. After outputting such an ultrasonic pulse U(t), the ultrasonic transducer 10 changes to the position of repose without excessive post-pulse oscillation, because of the disposition of the damping body 36, and the transducer is then ready to output a new ultrasonic pulse U(t). A further advantage that can be mentioned is that the housing (cup 28) need not be of a very expensive material, such as from the firm Dosey, as might actually be expected, but instead it can be fabricated from any arbitrary material, since the particular properties of these hard foams filled with hollow glass beads become important only in the resonant system (which is intentionally avoided herein). It has also been found that the "optimal" acoustical impedances need not be adhered to especially precisely, which makes the selection of materials easier.

I claim:

1. An ultrasonic transducer for measuring the travel time of ultrasonic pulses in a gas, comprising:
   a) a piezoelectric radial oscillator having two sides, electrodes each being disposed on a respective one of said sides for receiving a spike pulse voltage;
   b) a first adaptation layer being applied to one of said sides of said radial oscillator, said first adaptation layer having a thickness $d_A$ less than one-fourth of a characteristic wavelength of the transducer;
   c) a second adaptation layer applied to said first adaptation layer, said second adaptation layer also having a thickness $d_B$ less than one-fourth of the characteristic wavelength of the transducer, and said thicknesses $d_A$ and $d_B$ following the statement $d_A + d_B \approx \lambda/4$;
   d) a damping body mounted on the other of said sides of said radial oscillator; and e) said radial oscillator and said adaptation layers forming a sandwich executing a thickness oscillation as a consequence of a radial-thickness coupling, as soon as the spike pulse voltage is applied, and the characteristic wavelength of the transducer being a wavelength resulting from natural resonance in the thickness oscillation.

2. The ultrasonic transducer according to claim 1, wherein said piezoelectric radial oscillator is formed of a piezoceramic.

3. The ultrasonic transducer according to claim 1, wherein said first adaptation layer is in the form of a cup having a bottom, and said radial oscillator is disposed on said bottom of said cup.

4. The ultrasonic transducer according to claim 3, wherein said cup is filled with said damping body.

5. The ultrasonic transducer according to claim 3, wherein said cup has a flattened surface in the vicinity of said bottom.

6. The ultrasonic transducer according to claim 1, including a third adaptation layer disposed over said second adaptation layer.

7. The ultrasonic transducer according to claim 1, wherein said thickness $d_A$ of said first adaptation layer is selected as $$\lambda/8 \leq d_A < \lambda/4,$$

said thickness $d_B$ of said second adaptation layer is selected as $$\lambda/8 \leq d_B < \lambda/4, \text{ and}$$

$\lambda$ is the wavelength of the thickness oscillation.

8. The ultrasonic transducer according to claim 7, wherein said thicknesses $d_A$ and $d_B$ of said first and second adaptation layers follow the statement:

$$d_A + d_B \approx \lambda/4.$$

9. The ultrasonic transducer according to claim 7, wherein said thicknesses $d_A$ and $d_B$ of said first and second adaptation layers and the thickness $d_K$ of said radial oscillator follow the statement:

$$d_A + d_B + d_K \approx \lambda/2.$$

10. The ultrasonic transducer according to claim 8, wherein said thicknesses $d_A$ and $d_B$ of said first and second adaptation layers and the thickness $d_K$ of said radial oscillator follow the statement:

$$d_A + d_B + d_K \approx \lambda/2.$$

11. The ultrasonic transducer according to claim 1, wherein said first adaptation layer is a layer of glass microbeads in epoxy resin.

12. The ultrasonic transducer according to claim 1, wherein said second adaptation layer is an open-cell foam.

13. The ultrasonic transducer according to claim 1, including an electric excitation circuit for applying the spike pulse voltage to said electrodes, said electric excitation circuit including a capacitor discharging to said electrodes upon being activated.

14. The ultrasonic transducer according to claim 1, including an evaluation circuit evaluating at most a first three half-waves of each of the ultrasonic pulses tripped upon excitation, after each pulse passes through the gas.

15. The ultrasonic transducer according to claim 1, wherein a characteristic transducer frequency is approximately 200 kHz.

16. An ultrasonic transducer for measuring the travel time of ultrasonic pulses in a gas, comprising:

a) a piezoelectric radial oscillator having two sides, electrodes each being disposed on a respective one of said sides for receiving a spike pulse voltage;

b) a first adaptation layer applied to one of said sides of said radial oscillator, said first adaptation layer having a thickness $d_A$ defined as $$d_A < 0.2\lambda,$$

where $\lambda$ is a characteristic wavelength of the transducer;

c) a second adaptation layer applied to said first adaptation layer, said second adaptation layer having a thickness $d_B$ defined as $$d_B < 0.2\lambda;$$

d) a damping body mounted on the other of said sides of said radial oscillator; and e) said radial oscillator and said adaptation layers forming a sandwich executing a thickness oscillation as a consequence of a radial-thickness coupling, as soon as the spike pulse voltage is applied, and the characteristic wavelength of the transducer being a wavelength resulting from natural resonance in the thickness oscillation.

17. The ultrasonic transducer according to claim 16, wherein said thicknesses $d_A$ and $d_B$ of said first and second adaptation layers follow the statement:

$$d_A + d_B \leq \lambda/4.$$

* * * * *